Figure 1:
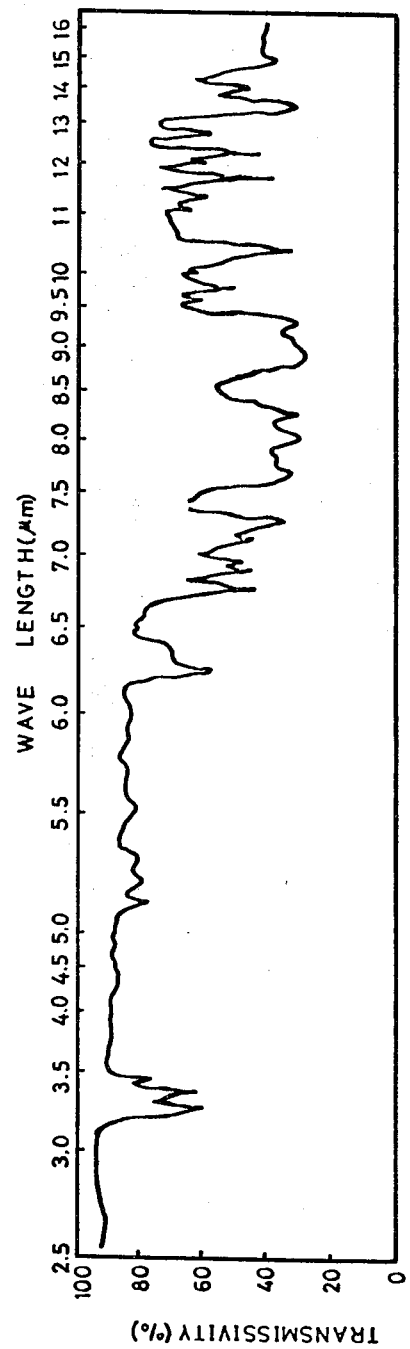

United States Patent [19]

Kobayashi et al.

[11] 4,423,259
[45] Dec. 27, 1983

[54] PROCESS FOR PRODUCING PHENYL-[3,3,3-TRIFLUOROPROPYL)-PHENYL]METHANE

[75] Inventors: Yoshiro Kobayashi, Tokyo; Itsumaro Kumadaki, Hachiohji; Masaaki Takahashi, Tokyo; Takashi Yamauchi, Iwaki, all of Japan

[73] Assignee: Kureha Kagaku Kogyo Kabushiki Kaisha, Tokyo, Japan

[21] Appl. No.: 347,728

[22] Filed: Feb. 10, 1982

Related U.S. Application Data

[62] Division of Ser. No. 233,715, Feb. 12, 1981, Pat. No. 4,356,335.

[30] Foreign Application Priority Data

| Feb. 22, 1980 [JP] | Japan | 55/21090 |
| Feb. 22, 1980 [JP] | Japan | 55/21091 |
| Feb. 22, 1980 [JP] | Japan | 55/21092 |
| Feb. 22, 1980 [JP] | Japan | 55/21093 |
| Feb. 22, 1980 [JP] | Japan | 55/21094 |
| Sep. 1, 1980 [JP] | Japan | 55/120928 |
| Nov. 21, 1980 [JP] | Japan | 55/164434 |

[51] Int. Cl.³ .................................................. C07C 17/26
[52] U.S. Cl. .................................. 570/144; 570/129; 570/127
[58] Field of Search ........................ 570/144, 129, 127

[56] References Cited

U.S. PATENT DOCUMENTS

| 2,680,770 | 6/1954 | Markarian | 570/129 |
| 3,080,428 | 3/1963 | Weinmayr | 570/127 |
| 3,106,587 | 10/1963 | Harms | 570/129 |
| 4,356,335 | 10/1982 | Koboyashi et al. | 570/129 |

*Primary Examiner*—John Doll
*Assistant Examiner*—Joseph A. Boska
*Attorney, Agent, or Firm*—Wegner & Bretschneider

[57] ABSTRACT

Novel trifluoropropyl-substituted aryl- or aralkylbenzene of the formula:

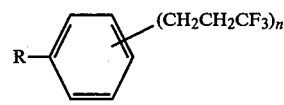

wherein R is a not-substituted or ring-substituted phenyl-, benzyl-, phenethyl- or alpha-methylbenzyl group by one 3,3,3-trifluoropropyl group, and n is an integer of 1,2 or 3, provided that the total number of 3,3,3-trifluoropropyl group of the above-mentioned trifluoropropyl-substituted aryl- or aralkylbenzene is at most 3, and a process for producing thereof are disclosed.

2 Claims, 12 Drawing Figures

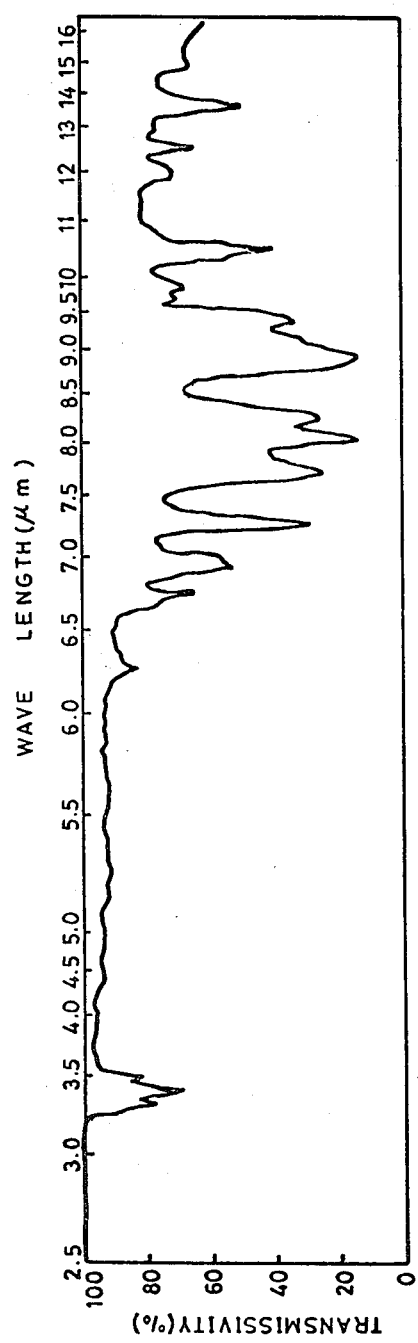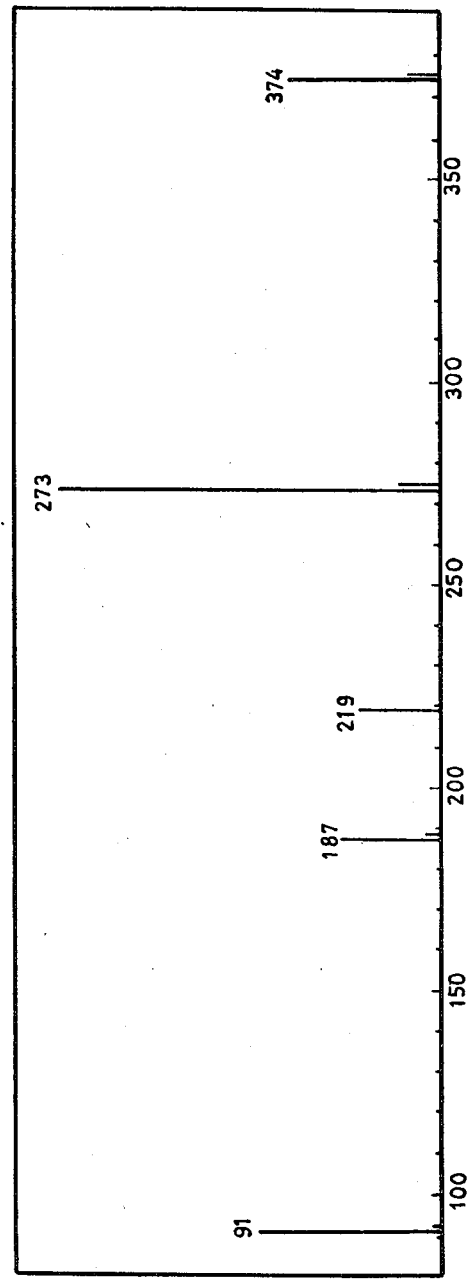

PROCESS FOR PRODUCING PHENYL-[3,3,3-TRIFLUOROPROPYL)-PHENYL]METHANE

This application is a divisional of application Ser. No. 233,715 filed Feb. 12, 1981, now U.S. Pat. No. 4,356,335.

BACKGROUND AND DETAILED DESCRIPTION OF THE INVENTION

The present invention relates to novel aryl- or aralkylbenzenes having two benzene rings at least one of which is substituted by at least one 3,3,3-trifluoropropyl group and also to a novel process for producing them. The aryl- or aralkylbenzene having two benzene rings at least one of which is substituted by at least one 3,3,3-trifluoropropyl group is expected to be, for example, dielectric materials.

As a means for synthesizing such an aromatic compounds having benzene ring substituted by 3,3,3-trifluoropropyl group, only one process has been proposed (U.S. Pat. No. 3,080,428), in which 3,3,3-trifluoropropyl ether, $(CF_3CH_2CH_2)_2O$, is brought into reaction with benzene in the presence of hydrogen fluoride to obtain (3,3,3-trifluoropropyl)benzene. However, since in the above-mentioned process, water is formed by the reaction, the activity of the catalyst is reduced during the reaction, and the recovery of once-used catalyst is difficult. Moreover, 3,3,3-trifluoropropyl ehter as the starting material is synthesized by the reaction of hydrogen fluoride, formaldehyde (or its polymer) and vinylidene fluoride. Accordingly, 3,3,3-trifluoropropyl ether is expensive because of the high price of vinylidene fluoride and of the yield of synthesizing the ether as low as 50 to 60%.

It is an object of the present invention to provide a trifluoropropyl derivative of aryl-or aralkylbenzene of the general formula:

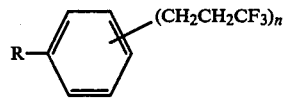

wherein R is a not-substituted or substituted phenyl group, benzyl group, phenethyl group or alpha-methylbenzyl group by 3,3,3-trifluoropropyl group and n is 1, 2 or 3, provided that the total number of 3,3,3-trifluoropropyl group in said trifluoropropyl derivative of aryl- or aralkylbenzene is at most 3. A further object is to provide a process for producing an aryl- or aralkylbenzene having at least one benzene ring substituted by at least one 3,3,3-trifluoropropyl group, which comprises bringing an aryl- or aralkylbenzene of the formula

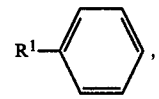

wherein $R^1$ represents phenyl group, benzyl group, phenethyl group or alpha-methylbenzyl group, into reaction with 3,3,3-trifluoropropylene in the presence of an acid catalyst, such as hydrogen fluoride or boron trifluoride. In addition, the reaction between biphenyl and 3,3,3-trifluoropropylene may also be carried out in the presence of a mixture of hydrogen fluoride and boron trifluoride as the catalyst.

Other object is to provide an dielectric material comprising at least one of 3,3,3-trifluoropropyl derivative of aryl- or aralkylbenzene. Another object is to provide a substituted aryl- or aralkylbenzene by 3,3,3-trifluoropropyl group obtained by bringing aryl- or aralkylbenzene into reaction with 3,3,3-trifluoropropylene in the presence of an acid catalyst, and separating said substituted aryl- or aralkylbenzene from the resultant reaction mixture. Still other objects and advantages of the present invention will become apparent hereinafter.

Figure 2:
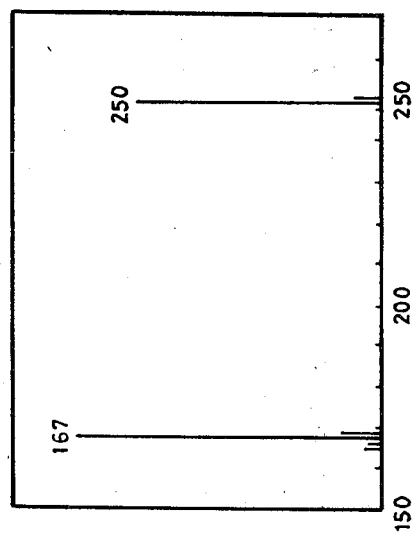
Figure 3:
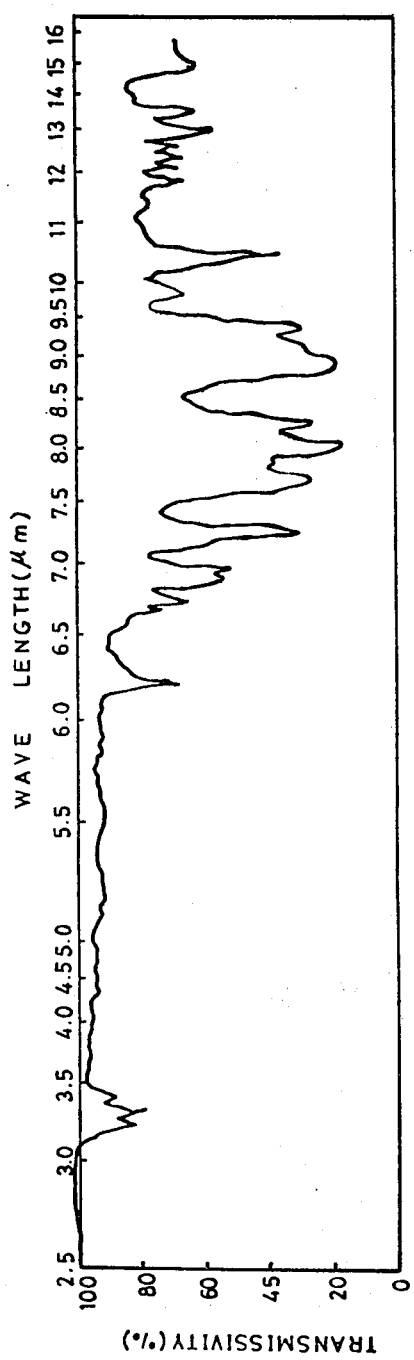
Figure 4:
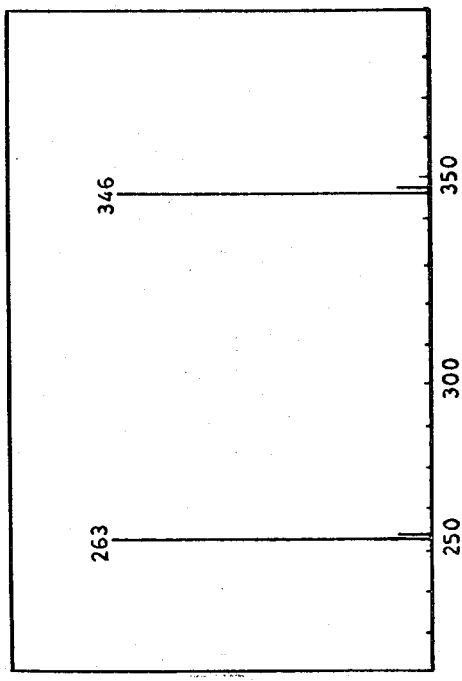
Figure 5:
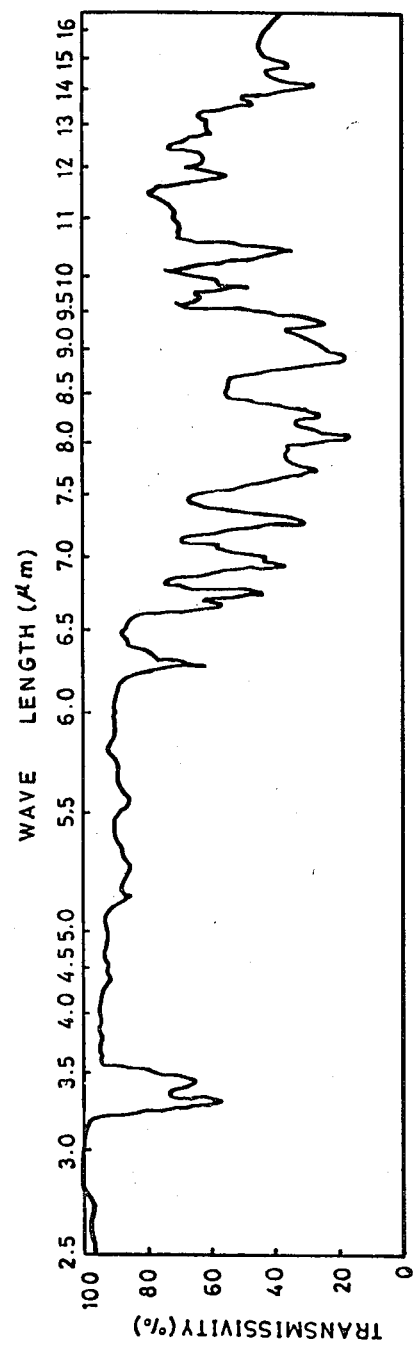
Figure 6:
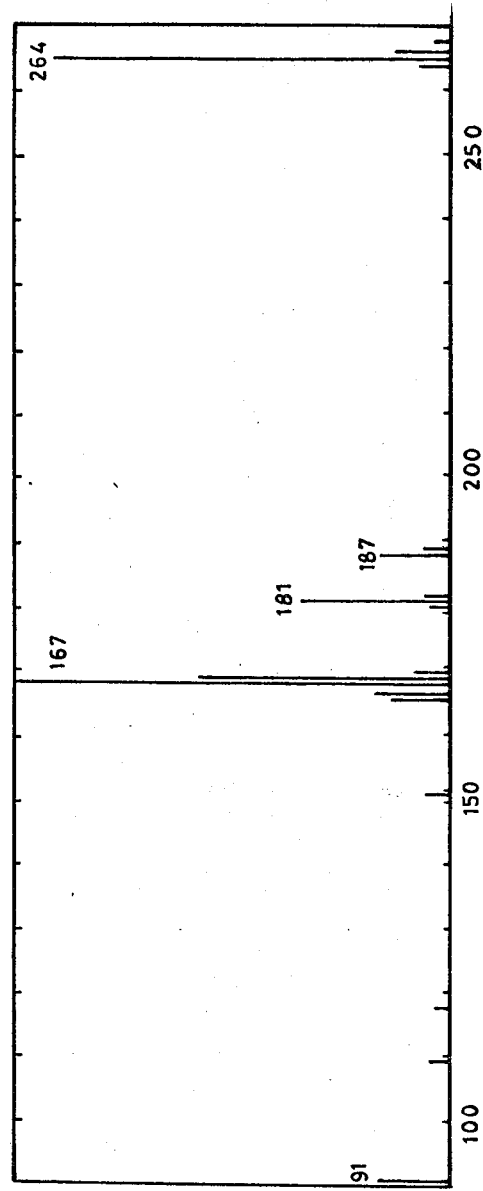
Figure 7:
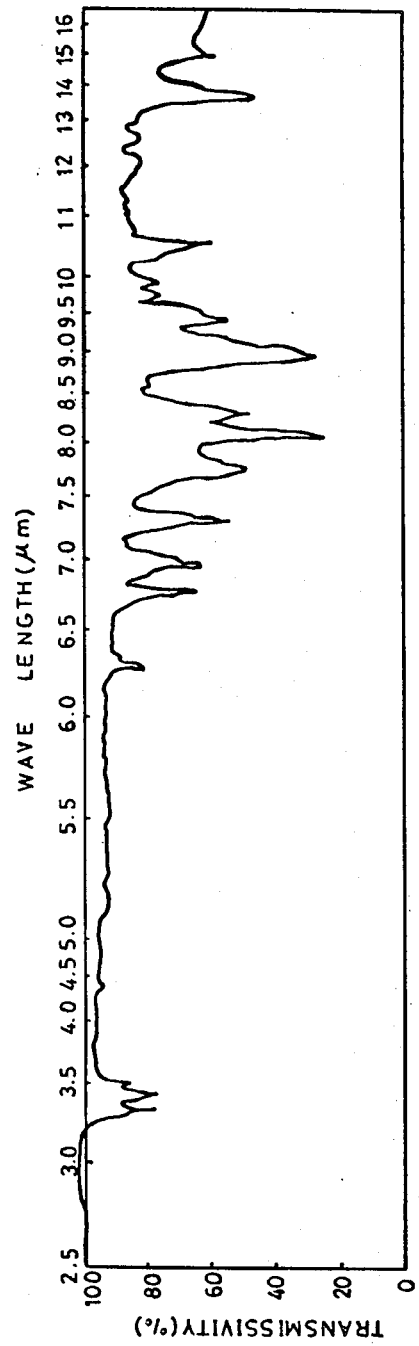
Figure 8:
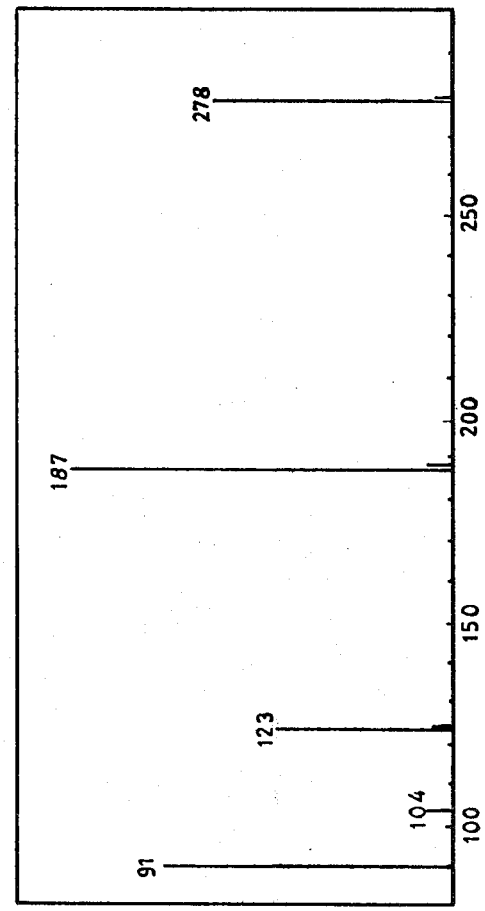
Figure 11:
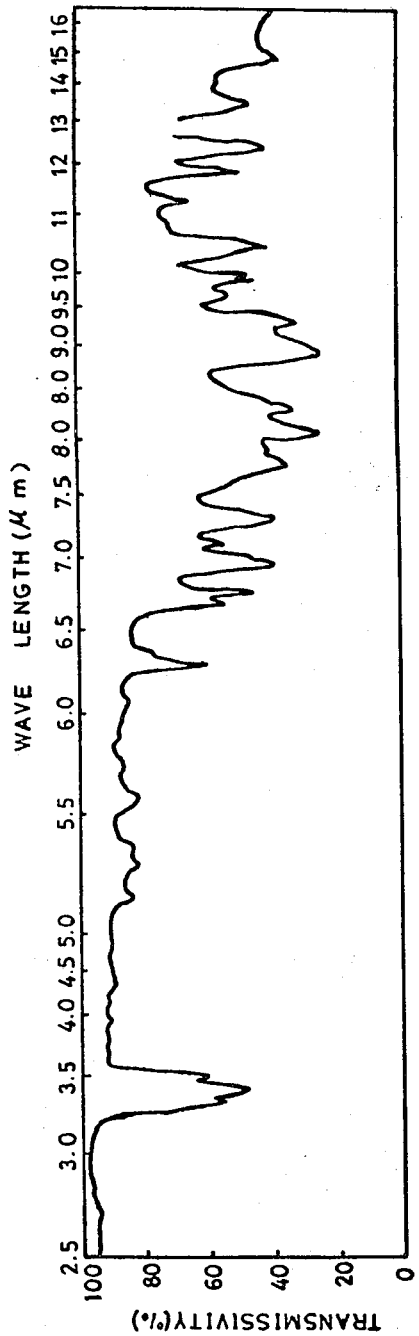
Figure 12:
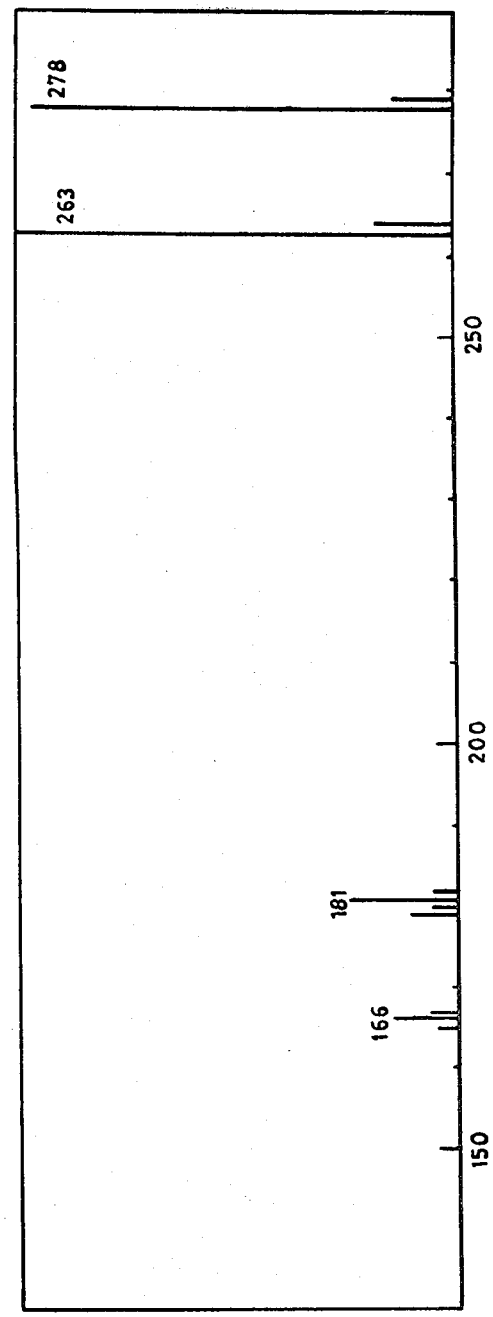

In the Drawing, FIGS. 1 and 2 show the infrared absorption spectrum and the mass spectrum, respectively of (3,3,3-trifluoropropyl)biphenyl; FIGS. 3 and 4 show those, respectively of biphenyl di-substituted by 3,3,3-trifluoropropyl groups; FIGS. 5 and 6 show those, respectively of diphenylmethane mono-substituted by 3,3,3-trifluoropropyl group; FIGS. 7 and 8 show those, respectively of 1,2-diphenylethane mono-substituted by 3,3,3-trifluoropropyl group; FIGS. 9 and 10 show those, respectively of 1,2-diphenylethane di-substituted by 3,3,3-trifluoropropyl groups and FIGS. 11 and 12 show those, respectively of 1,1-diphenylethane mono-substituted by 3,3,3-trifluoropropyl group.

Th aryl- or aralkylbenzenes having two benzene rings at least one of which is substituted by at least one 3,3,3-trifluoropropyl group according to the present invention are novel chemical compounds and will be used for a variety of purposes.

Furthermore, the above-mentioned mono-substituted aryl- or aralkylbenzene by 3,3,3-trifluoropropyl group according to the present invention are desirably biodegradable.

The concrete examples of synthesis of the novel trifluoropropyl derivatives of the present invention are described in Table 1, however, the syntheses of such derivatives are not confined therein.

TABLE 1

Examples of synthesizing the trifluoropropyl derivatives of arylbenzene or aralkylbenzene of the present invention

[A] 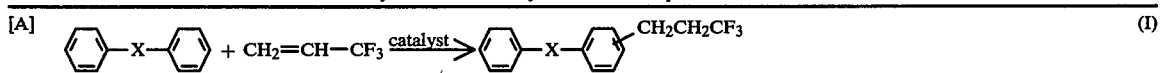 (I)

[B] 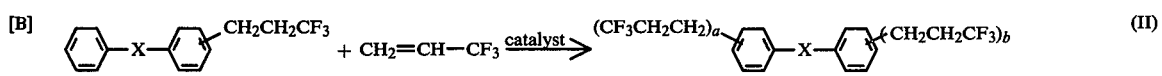 (II)

[C] 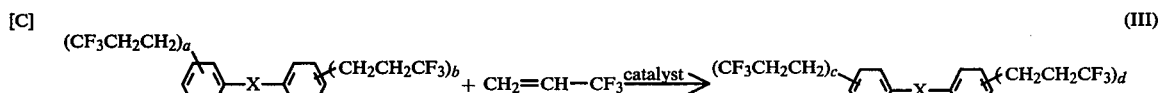 (III)

TABLE 1-continued
Examples of synthesizing the trifluoropropyl derivatives of arylbenzene or aralkylbenzene of the present invention wherein  (i) a = 0 and b = 2, or (ii) a = b = 1 in the reaction formula (II);
 (ii) c = 0 and d = 3, or (iv) c = 1 and d = 2 in the reaction formula (III); and further
 X means (A) a direct bonding between the two benzene rings namely the parent compound being diphenyl,
 (B) a methylene group, i.e., —CH$_2$—, namely the parent compound being diphenylmethane.
 (C) an ethylene group, i.e., —CH$_2$—CH$_2$—, namely the parent compound being 1,2-diphenylethane, or
 (D) a methylmethylene group, i.e., —CH(CH$_3$)—, namely the parent compound being 1,1-diphenylethane.

In addition, there is a reaction giving the same product as in (I) wherein X is a methylene group, as follows:

[D] 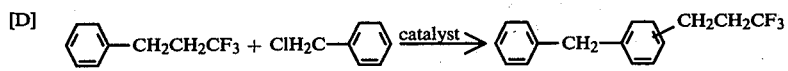

Since the trifluoropropyl derivatives of the present invention are excellent in electric properties, such as insulating property and dielectric property, they are possibly utilized as an insulating oil such as the insulating oil in capacitor, the above-mentioned specific properties of the derivatives of the present invention being presumed due to its trifluoropropyl group.

The process for synthesizing the compound of the present invention is described as follows: Generally, the compound of the present invention is synthesized by bringing the corresponding aromatic compound into reaction with 3,3,3-trifluoropropylene in the presence of an acid catalyst.

In the afore-mentioned reactions, since 3,3,3-trifluoropropylene (CF$_3$-CH=CH$_2$) used in the present invention has a strongly electron-withdrawing group, -CF$_3$, the basicity of the C-C double bond within the molecule of 3,3,3-trifluoropropylene is weaker than the basicity of the non-substituted parent compound, propylene (CH$_3$-CH=CH$_2$). Accordingly, in the reaction of 3,3,3-trifluoropropylene and an aromatic compound such as aryl- or aralkylbenzene, the presence of a strongly acidic Friedel-Crafts catalyst is necesary. However, in the case where one of the representative Friedel-Crafts catalyst, for example, anhydrous aluminum chloride is used, substitution of aromatic ring by chlorine atom and cyclization of the starting material are caused by the catalyst. On the other hand, anhydrous ferric chloride which is weaker than anhydrous aluminum chloride is almost inactive in the present reaction. Even if a silica-alumina catalyst is used, the desired compound is available only in a poor yield because of the occurence of various side reactions.

As a result of keen efforts of finding the appropriate catalyst for smoothly carrying out the present reaction, the inventors of the present invention have found out that hydrogen fluoride, boron trifluoride and a mixture thereof are effective in the present reaction. Since the catalyst for use in the present invention is a gas in normal state or a low-boiling liquid, the removal of the catalyst after ending the reaction is simply effected by stripping, and accordingly, the recovery and the reuse of the recovered catalyst are easily performed. In practicizing the process of the present invention, the catalyst is preferably used in an amount of more than 0.5 mole per mole of the aromatic compound as the starting material.

The reaction temperature depends upon the species of the startng material and the catalyst, and from the viewpoint of the species and activity of the catalyst, the temperature at which a catalyst shows its activity is highest in the case of hydrogen fluoride followed by boron trifluoride and then by mixtures of hydrogen fluoride and boron trifluoride.

Among the aromatic compounds used in the present invention as the starting material, although biphenyl is relatively stable in the reaction system of the process of the present invention, diphenylmethane and diphenylethanes may be decomposed in some cases where the reaction conditions are severe enough. Accordingly, the suitable reaction temperature depends upon the species of the starting material and the catalyst, and the preferable reaction temperature is, for example, −20° to 100° C. in the case of a mixture of hydrogen fluoride and boron trifluoride, 0° to 120° C. in the case of boron trifluoride and 50° and 150° C. in the case of hydrogen fluoride as the catalyst. At such a reaction temperature, the reaction completes within one to 30 hours.

While the product of the present reaction between propylene and an aromatic compound is an aromatic compound substituted by isopropyl group, (CH$_3$)$_2$CH-, the product of the present reaction between 3,3,3-trifluoropropylene and an aromatic compound is an aromatic compound substituted by 3,3,3-trifluoropropyl group, CF$_3$CH$_2$CH$_2$-, this fact having been confirmed by $^1$H-NMR- and $^{19}$F-NMR spectra.

After the reaction is over, the unreacted gas is purged and the remained catalyst is removed by means of stripping, neutralizing or washing, and the reaction product is obtained by distillation under reduced pressure.

In the last-mentioned reaction in Table 1:

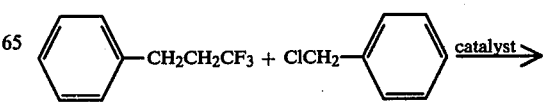

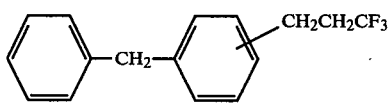

the starting material used in the afore-mentioned reaction, (3,3,3-trifluoropropyl)benzene is, as has been described in Japanese Patent Application 21094/80, for example, obtained by bringing benzene and 3,3,3-trifluoropropylene into reaction in the presence of hydrogen fluoride, boron trifluoride or a mixture thereof. Also the catalyst used in the afore-mentioned reaction, i.e., the reaction between (3,3,3-trifluoropropyl)benzene and benzyl chloride is carried out in the presence of a Friedel-Crafts catalyst. For example, aluminum chloride, ferric chloride, antimony pentachloride and sulfuric acid, and as a solid acid catalyst, silica-alumina and synthetic zeolite are possibly used.

The above-mentioned reaction can be carried out continuously or in batch wise under relatively mild reaction conditions of temperature and pressure. The following is an example of batch wise case.

Into a reaction vessel provided with a stirrer, a thermometer and a reflux condenser, (3,3,3-trifluoropropyl)benzene and a catalyst are introduced, and while maintaining them at a predetermined temperature, benzyl chloride is dropped into the vessel. The reaction temperature is desirably 0° to 50° C. when a metal chloride is used as the catalyst and 90° to 150° C. when a solid acid catalyst is used.

In either case, the reaction is carried out under ordinary pressure. The preferable amount of the catalyst is 0.2 to 2.0% by weight of (3,3,3-trifluoropropyl)benzene in the case of a metal chloride, and 5 to 20% by weight in the case of a solid acid catalyst. The reaction completes within one to 10 hours under the above-mentioned conditions.

After the reaction is over, the catalyst is removed from the reaction mixture by filtration or washing with water depending on the catalyst used, and then the reaction mixture is distilled to obtain phenyl-(3,3,3-trifluoropropyl)phenylmethane as a colourless and transparent liquid.

The product of the present invention, an aromatic compound substituted by trifluoropropyl has a high dielectric constant, a high insulating resistance and a low dielectric loss, and accordingly is possibly used as an insulating oil.

The present invention is more concretely explained while referring to non-limitative examples as follows:

EXAMPLE 1

Synthesis of biphenyl substituted by trifluoropropyl group(s)

In a stainless steel autoclave of a capacity of one liter, 385 g (2.50 mol) of biphenyl, 50 g (2.50 mol) of anhydrous hydrogen fluoride, 275 g (2.86 mol) of 3,3,3-trifluoropropylene and 15 g (0.22 mol) of boron trifluoride were introduced in the above-mentioned order, and brought into reaction while stirring at 60° C. for 15 hours.

After the reaction was over, the residual gas in the autoclave was purged and the liquid reaction mixture was washed with an aqueous alkaline solution and water to remove the catalyst. The gas-chromatographical analysis of the thus obtained reaction mixture revealed the following results shown in Table 2: Mass spectroscopy of the fractions of gas chromatography, and nuclear magnetic resonance spectroscopy or $^1H$ and $^{19}F$ fractions served for identification of each fraction appearing as a peak in gas chromatography.

TABLE 2

| Component | Composition (% by weight) of the volatile substance obtained from peak area in gas-chromatogram |
|---|---|
| Monosubstituted biphenyl by 3,3,3-trifluoropropyl group | 38.8 |
| Disubstituted biphenyl by 3,3,3-trifluoropropyl group | 21.2 |
| Trisubstituted biphenyl by 3,3,3-trifluoropropyl group | 6.7 |
| Tetrasubstituted biphenyl by 3,3,3-trifluoropropyl group | 2.0 |
| Biphenyl (not substituted) | 31.3 |

The above-mentioned mixture was subjected to distillation under reduced pressure to obtain a fraction boiling at 117° to 122° C./2 mmHg. It was confirmed by the analytical data shown below and gas chromatogram that the fraction contained a novel compound of (3,3,3-trifluoropropyl)biphenyl in an amount of higher than 99%.

(a) Mass spectrographical analysis at 20 eV: (m/e) 250 The mass spectrogram is shown in FIG. 2.

(b) Nuclear magnetic resonance spectrometry:

In $^1H$-NMR spectrum, no signal of methyl group was observed, and only the signals of aromatic proton and methylene group were observed, respectively. On the other hand, in $^{19}F$-NMR spectrum, a signal of trifluoromethyl group was observed from that of benzotrifluoride to the neighbourhood of +3.92 ppm as a triplet.

| (c) Elementary analysis: | C (%) | H (%) | F (%) |
|---|---|---|---|
| Found | 71.6 | 5.2 | 23.2 |
| Calcd. as $C_{15}H_{13}F_3$ | 72.0 | 5.2 | 22.8 |

(d) Infrared absorption spectrometry: The infrared absorption spectrogram was shown in FIG. 1.

The electrical properties of (3,3,3-trifluoropropyl)-biphenyl at 20° C. are shown in Table 3.

TABLE 3

| Dielectric constant | 5.1 |
|---|---|
| Dielectric loss (tan δ) (%) | 0.02 to 0.03 |
| Volume resistivity (Ω · cm) | $9.3 \times 10^{13}$ |

TEST OF BIODEGRADABILITY

The biodegradability of (3,3,3-trifluoropropyl)biphenyl was examined by using the standard activated sludge of Japanese Society of Examination of Chemicals as follows.

The above-mentioned activated sludge and (3,3,3-trifluoropropyl)biphenyl were added to a basic culture medium comprising inorganic salts so that the concentrations of the active sludge and the compound were 100 ppm, respectively, and the thus adjusted culture medium was cultured in a shaking flask. The gas-chromatographical analysis of the medium after 14 day-culture showed the absence of (3,3,3-trifluoropropyl)-biphenyl in the cultured medium.

EXAMPLE 2

By distillation of the reaction mixture obtained in Example 1 under a reduced pressure, a fraction boiling at 144° to 148° C./2 mm Hg was obtained. It was confirmed from the following analytical data shown below and gas chromatogram that the fraction contained a novel compound, bis(3,3,3-trifluoropropyl)biphenyl, in an amount of higher than 99%.

(a) Mass spectrographical analysis at 20 eV: (m/e) 346 The mass spectrum of the fraction is shown in FIG. 4.

(b) Nuclear megnetic resonance spectrometry: The results of NMR spectrometry were similar to that of (3,3,3-trifluoropropyl)biphenyl in Example 1.

(c) Elementary analysis:

|  | C (%) | H (%) | F (%) |
| --- | --- | --- | --- |
| Found | 62.8 | 4.4 | 32.8 |
| Calcd. as $C_{15}H_{13}F_3$ | 62.4 | 4.6 | 33.0 |

(d) Infrared absorption spectrometry:

The infrared absorption spectrum of the fraction is shown in FIG. 3.

The electrical properties of bis(3,3,3-trifluoropropyl)-biphenyl at 20° C. are shown in Table 4.

TABLE 3

| Dielectric constant | 5.0 |
| --- | --- |
| Dielectric loss (tan δ) (%) | 0.03 |
| Volume resistivity (Ω · cm) | $6.5 \times 10^{13}$ |

EXAMPLE 3

Into a 20-ml stainless steel reaction tube, 2 g of biphenyl, one milliliter of anhydrous hydrogen fluoride and 2.7 g of 3,3,3-trifluoropropylene were introduced in the above-mentioned order, and after sealing the tube, it was heated to 100° C. and kept at the temperature for 21 hours to bring the content into reaction. After the reaction was over, the content of the autoclave was neutralized, washed with water and dried following the ordinary method. The results of gas-chromatographical examination of the reaction mixture are shown in Table 5.

TABLE 5

| Component | Composition (% by weight) obtained by peak area of gas-chromatogram |
| --- | --- |
| Monosubstituted biphenyl by 3,3,3-trifluoropropyl group | 35.3 |
| Disubstituted biphenyl by 3,3,3-trifluoropropyl group | 30.9 |
| Trisubstituted biphenyl by 3,3,3-trifluoropropyl group | 11.3 |
| Tetrasubstituted biphenyl by 3,3,3-trifluoropropyl group | 4.1 |
| Biphenyl (not substituted) | 18.4 |

EXAMPLE 4

Into a 20-ml stainless steel reaction tube, one gram of biphenyl was introduced and further 2 g of 3,3,3-trifluoropropylene was introduced, and then boron trifluoride was pressured into the tube so that the internal pressure of the tube showed 4.5 kg/cm².gauge. The reaction tube was immersed into an oil bath at 80° C. for 17.5 hours. Then the content liquefied at that time was washed with water and dried. The results of gas-chromatographical examination of the reaction mixture thus obtained are shown in Table 6.

TABLE 6

| Component | Composition (% by weight) obtained by peak area of gas-chromatogram |
| --- | --- |
| Monosubstituted biphenyl by 3,3,3-trifluoropropyl group | 57.6 |
| Disubstituted biphenyl by 3,3,3-trifluoropropyl group | 12.2 |
| Trisubstituted biphenyl by 3,3,3-trifluoropropyl group | 0.5 |
| Biphenyl (not substituted) | 29.7 |

EXAMPLE 5

Synthesis of substituted diphenylmethane by 3,3,3-trifluoropropyl group(s)

Into a one-liter four-necked flask provided with a stirrer, a reflux condenser and a thermometer, 261 g (1.5 mol) of (3,3,3-trifluoropropyl)benzene and 2.6 g of ferric chloride were introduced, and while stirring the content at a room temperature of 26° C., 95 g (0.75 mol) of benzyl chloride was dropped into the flask within 2 hours. After continuing the stirring further for 2 hours, the content of the flask was washed with water and dried. The results of the gas-chromatographical examination of the thus obtained reaction mixture amounting to 318 g are shown in Table 7.

TABLE 7

| Component | Composition (% by weight) obtained by the peak area of gas-chromatogram |
| --- | --- |
| Monosubstituted diphenylmethane by 3,3,3-trifluoropropyl group | 31.6 |
| 3,3,3-trifluorobenzene disubstituted by benzyl group | 10.5 |
| 3,3,3-trifluoropropylbenzene (unreacted) | 57.9 |
| Benzyl chloride (unreacted) | trace |

In the next place, the thus obtained reaction mixture was subjected to distillation under reduced pressure to collect a fraction boiling at 122° to 125° C./2 mmHg. The fraction contained more than 99% of a novel compound, (3,3,3-trichloropropyl)phenylphenylmethane, the fact being confirmed by gas chromatogram and the following analytical data:

(a) Mass spectrometry at 20 eV: (m/e) 264 The mass spectrogram is shown in FIG. 6.

(b) Nuclear magnetic resonance spectroscopy: In its ¹H-NMR spectrogram, no signal due to methyl group was observed. On the other hand, in its ¹⁹F-NMR spectrum, the signal of trifluoromethyl group was observed in the neighbourhood position of +2.6 ppm as a triplet from that of benzotrifluoride as an internal standard.

(c) Elementary analysis:

|  | C (%) | H (%) | F (%) |
| --- | --- | --- | --- |
| Found | 72.8 | 5.4 | 21.8 |
| Calcd. as $C_{16}H_{15}F_3$ | 72.7 | 5.7 | 21.6 |

(d) Infrared absorption spectroscopy:

The infrared absorption spectrum of the fraction is shown in FIG. 5.

The fraction showed a specific gravity of 1.128 at 27° C., and a refractive index of $n_D^{25}$ of 1.511.

The electrical properties of the fraction at 20° C. are shown below in Table 8:

TABLE 8

| | |
|---|---|
| Dielectric constant | 4.77 |
| Dielectric loss (tan δ) (%) | 0.27 |
| Volume resistivity (Ω · cm) | $1.35 \times 10^{14}$ |

EXAMPLE 6

In the same flask as in Example 5, 261 g (1.5 mol) of (3,3,3-trifluoropropylene)benzene, 36 g of a silica-alumina catalyst (N-633 L, manufactured by Nikki Kagaku Co., Ltd., Japan) were introduced, and while stirring the content of the flask at 120° C., 95 g (0.75 mol) of benzyl chloride was dropped into the flask within 2 hours. After the addition of benzyl chloride, stirring was continued further for 2 hours and the dissolved hydrogen chloride was neutralized by the addition of powdery sodium carbonate. By filtering the neutralized reaction mixture, an almost colourless and transparent liquid was obtained. The gas-chromatographical analytical data of the liquid are shown in Table 9.

TABLE 9

| Component | Composition (% by weight) obtained by peak area in the gas-chromatogram |
|---|---|
| Monosubstituted diphenylmethane by 3,3,3-trifluoropropyl group | 25.4 |
| 3,3,3-trifluoropropylbenzene disubstituted by benzyl group | 8.3 |
| Unreacted 3,3,3-trifluoropropyl-benzene | 66.3 |
| Unreacted benzyl chloride | trace |

EXAMPLE 7

Into a 200-ml stainless steel autoclave, 70 g of diphenylmethane and 48 g of 3,3,3-trifluoropropylene were introduced, and further, boron trifluoride was pressured into the autoclave so that the internal pressure showed 50 kg/cm² gauge. The content of the autoclave was brought into reaction at 10° C. for 20 hours. After that, the content was collected and following the ordinary method, it was washed with water and dried. The results of examination of the reaction mixture by gas-chromatography are shown in Table 10. The boiling point of monosubstituted diphenylmethane by 3,3,3-trifluoropropyl group was 129° to 132° C./3 mmHg.

TABLE 10

| Composition of the reaction mixture as revealed by comparison if the area of peaks in chromatogram | |
|---|---|
| Component | Composition (% by weight) (refer to Table 2) |
| Benzene | 0.2 |
| (3,3,3-trifluoropropyl)benzene | 0.1 |
| Unreacted diphenylmethane | 49.2 |
| Monosubstituted diphenylmethane by 3,3,3-trifluoropropyl group | 42.7 |
| Disubstituted diphenylmethane by 3,3,3-trifluoropropyl group | 7.7 |
| Trisubstituted diphenylmethane by 3,3,3-trifluoropropyl group | 0.1 |

COMPARATIVE EXAMPLE 1

Into a 5-ml stainless steel reaction tube, 1 g of diphenylmethane and 0.6 g of 3,3,3-trifluoropropylene were introduced, and further boron trifluoride was pressured into the tube so as to make the internal pressure of the tube to 5 kg/cm².gauge. Then, the tube was put into an oil bath at 130° C. and kept therein for 17 hours to stand still. After the reaction was over, the content of the tube was treated following the ordinary method, and the treated reaction mixture was analyzed by gas chromatography to find out the following results shown in Table 11. As is seen in Table 11, it was found that a disproportionation has taken place.

TABLE 11

| Composition of the reaction mixture | |
|---|---|
| Component | Composition (% by weight) obtained by comparing the areas of peaks in the gas chromatogram |
| Monosubstituted diphenylmethane by trifluoropropyl group | 2.59 |
| Monosubstituted diphenylmethane by benzyl group | 0.9 |
| Unsubstituted diphenylmethane | 95.95 |
| Benzene | 0.56 |

COMPARATIVE EXAMPLE 2

Into a 300-ml stainless steel autoclave, 10 g of diphenylmethane, 50 g of decahydronaphthalene, 6 g of 3,3,3-trifluoropropylene and 1 g of ferric chloride were introduced, and they were brought into reaction at 90° C. for 4 hours. However, in the present case, no product substituted by 3,3,3-trifluoropropyl group was obtained from the reaction mixture.

EXAMPLE 8

Synthesis of 1,2-diphenylethane substituted by trifluoropropyl group(s):

In the same autoclave as in Example 1, 364 g (2.00 mol) of 1,2-diphenylethane, 222 g (2.31 mol) of 3,3,3-trifluoropropylene were introduced, and further boron trifluoride was pressured into the autoclave so that the internal pressure became 61 kg/cm².G. The content of the autoclave was brought into reaction while stirring for 19 hours at 60° C. Then, the residual gas in the autoclave was purged, and the content therein was washed with water and dried following the ordinary method to obtain 542 g of the reaction mixture. The results of analysis, the composition of the mixture, by gas chromatography are shown in Table 12.

TABLE 12

| Component | Composition (% by weight) (refer to Table 2) |
|---|---|
| Monosubstituted 1,2-diphenylethane by 3,3,3-trifluoropropyl group | 51.2 |
| Disubstituted 1,2-diphenylethane by 3,3,3-trifluoropropyl group | 25.8 |
| Trisubstituted 1,2-diphenylethane by 3,3,3-trifluoropropyl group | 3.1 |
| Unreacted 1,2-diphenylethane | 19.8 |

By subjecting the above-mentioned reaction mixture to a fine distillation under a reduced pressure, a fraction boiling at 125° to 128° C./1 mmHg was obtained. That the fraction contained more than 99% of a novel compound, 1-phenyl-2-(3,3,3-trifluoropropyl)phenylethane, was confirmed by gas chromatogram and the following results of analyses:

(a) Mass spectrography at 20 eV: (m/e) 278. The mass spectrum of the fraction is shown in FIG. 8.

(b) Nuclear magnetic resonance spectrography: In the spectrum of $^1$H-NMR, no signal due to methyl group was observed, and on the other hand, in the $^{19}$F-NMR spectrum, a signal due to trifluoromethyl group was observed in the neighbourhood of positions 4.16 and 3.94 ppm from that of benzotrifluoride as an internal standard as the overlap of two kinds of triplet.

(c) Elementary analysis:

|  | C (%) | H (%) | F (%) |
| --- | --- | --- | --- |
| Found | 73.6 | 5.8 | 20.6 |
| Calcd. as $C_{17}H_{17}F_3$ | 73.4 | 6.1 | 20.5 |

(d) Infrared absorption spectroscopy: The infrared absorption spectrum of the fraction is shown in FIG. 7.

The fraction showed a specific gravity of $d_4^{15}$ of 1.1299, a refractive index of $n_D^{25}$ of 1.5078 and kinematic viscosities of 6.72 and 1.62 cSt, respectively at 100° F. and 210° F.

The data shown in Table 13 are the electric properties of the fraction.

TABLE 13

| Dielectric constant | 4.49 |
| --- | --- |
| Dielectric loss (tan δ) (%) | 0.02 |
| Volume resistivity (Ω · cm) | $1.14 \times 10^{14}$ |

The biodegradability of the fraction was examined in the same manner as in Example 1, and the result was the negativity of the fraction in the 14-day culture with the standard sludge in gas chromatography. The result shows the desirable biodegradability of the fraction substantially composed of 1-phenyl-2-[(3,3,3-trifluoropropyl)phenyl]ethane.

EXAMPLE 9

By subjecting the reaction mixture obtained in Example 8 to fine distillation at a reduced pressure of 1 mmHg, a fraction boiling at 145° to 150° C. at the pressure. That the fraction contains more than 99% of a novel compound, disubstituted 1,2-diphenylethane by 3,3,3-trifluoropropyl group, was confirmed by the following analytical data and chromatogram:

(a) Mass spectrography at 20 eV: (m/e) 374

(b) Nuclear magnetic resonance spectrometry: The situation was the same as in Example 8.

(c) Elementary analysis:

|  | C (%) | H (%) | F (%) |
| --- | --- | --- | --- |
| Found | 73.6 | 5.8 | 20.6 |
| Calcd. as $C_{20}H_{20}F_6$ | 73.4 | 6.1 | 20.5 |

(d) Infrared absorption spectroscopy:

The infrared absorption spectrum of the fraction is shown in FIG. 9.

The fraction showed a specific gravity of $d_4^{15}$ of 1.2142 and a refractive index of $n_D^{25}$ of 1.4780, and kinematic viscosities of 18.45 cSt and 2.78 cSt, respectively at 100° F. and 210° F.

The data shown in Table 15 are the electrical properties of the fraction at 20° C.

TABLE 14

| Dielectric constant | 5.57 |
| --- | --- |
| Dielectric loss (tan δ) (%) | 0.01 |
| Volume resistivity (Ω · cm) | $1.64 \times 10^{14}$ |

EXAMPLE 10 in the same tube as in Example 3, 2.4 g of 1,2-diphenylethane, 5 ml of anhydrous hydrogen fluoride and 2 g of 3,3,3-trifluoropropylene were introduced, and by heating the tube at 100° C., the content was brought into reaction for 17 hours. After the reaction was over, the reaction mixture was neutralized, washed with water and dried following the ordinary method. The gas chromatographical analytical data (the composition) of the treated reaction mixture are shown in Table 15.

TABLE 15

| Component | Composition (% by weight) (refer to Table 2) |
| --- | --- |
| Monosubstituted 1,2-diphenylethane by 3,3,3-trifluoropropyl group | 24.5 |
| Disubstituted 1,2-diphenylethane by 3,3,3-trifluoropropyl group | 2.0 |
| Monosubstituted 1,2-diphenylethane, however, by benzyl group | 0.7 |
| Unsubstituted 1,2-diphenylethane | 72.5 |

COMPARATIVE EXAMPLE 3

The same procedures as in Example 8 were carried out except for adopting the catalyst of the mixture of hydrogen fluoride and boron trifluoride and the reaction temperature of 60° C. As a result, decomposition of the skeleton of 1,2-diphenylethane took place to give a complicated pattern in the gas chromatogram of the reaction mixture thus obtained. The composition of the reaction mixture determined by comparing the respective areas of the peaks appearing in the gas chromatogram is shown in Table 16.

TABLE 16

| Component | Composition (% by weight) (refer to Table 2) |
| --- | --- |
| Monosubstituted 1,2-diphenylethane by 3,3,3-trifluoropropyl group | 7.7 |
| Disubstituted 1,2-diphenylethane by 3,3,3-trifluoropropyl group | 2.5 |
| Unreacted 1,2-diphenylethane | minute amount |
| Benzene | 18.9 |
| 3,3,3-trifluoropropylbenzene | 9.9 |
| bis(3,3,3-trifluoropropyl)benzene | 19.7 |
| tris(3,3,3-trifluoropropyl)benzene | 27.5 |
| tetrakis(3,3,3-trifluoropropyl)benzene | 4.5 |

EXAMPLE 11

Synthesis of 1,1-diphenylethanes substituted by 3,3,3-trifluoropropyl group(s)

Into the same autoclave as in Example 1, 240 g (of 1,1-diphenylethane and 127 g of 3,3,3-trifluoropropylene were introduced, and boron trifluoride was pressured into the autoclave so that the internal pressure of the autoclave became to 60 kg per cm².gauge. The content of the autoclave was brought into reaction at room temperature for 20 hours. After the reaction was over, the residual gas was purged, and after extracting the content of the autoclave with dichloromethane, the extract was washed with water and dried following the ordinary method, and then dichloromethane was distilled off. The thus obtained reaction mixture was subjected to fine distillation under a reduced pressure to obtain a fraction boiling at 118° to 120° C./1 mmHg.

According to the gas chromatographical examination and the following analytical results, the above-mentioned fraction was confirmed to contain more than 99% of a compound, 1-phenyl-1-[(3,3,3-trifluoropropyl)phenyl]ethane:

(a) Mass spectrograhy at 20 eV: (m/e) 278 The mass spectrogram of the fraction is shown in FIG. 12.

(b) Nuclear magnetic resonance spectroscopy: In the $^1$H-NMR spectrum: in carbon tetrachloride:
δ(ppm)
2.63(d) (-CH$_3$(3H)J=7.0 Hz)
1.9-3.0 (m) (-CH$_2$-(4H)
4.10(q) (-CH-(1H)J=7.0 Hz)
6.9-7.0 (Hydrogen atom on benzene ring (9H)

In the $^{19}$F-NMR spectrum:
A signal of trifluoromethyl group was observed as a triplet on the position +2.5 ppm from the signal of benzotrifluoride as the internal standard.

| (c) Elementary analysis: | | | |
|---|---|---|---|
| | C (%) | H (%) | F (%) |
| Found | 73.3 | 6.0 | 20.7 |
| Calcd. as C$_{17}$H$_{17}$F$_3$ | 73.4 | 6.1 | 20.5 |

(d) Infrared absorption spectroscopy:
The infrared absorption of the fraction is shown in FIG. 11.

The above-mentioned fraction showed a specific gravity of d$_4^{20}$ of 1.116 and a refractive index of n$_D^{20}$ of 1.5121.

The following data are the electric properties of the fraction at 20° C.

| Dielectric constant | 4.60 |
|---|---|
| Dielectric loss (tan δ) (%) | 0.067 |
| Volume resistivity (Ω · cm) | 1.20 × 10$^{14}$ |

EXPERIMENTAL EXAMPLE

Into an autoclave made of stainless steel having a capacity of 1 l, 273 g of benzene, 72 g of anhydrous hydrogen fluoride and 364 g of 3,3,3-trifluoropropylene were introduced in the order, and while cooling the reaction tube with a mixture of dry-ice and methanol, boron trifluoride was pressured into the tube so that the internal pressure of the tube became 10 kg/cm$^2$.G. Then the tube was kept at a temperature of 20° C. to bring the content into reaction, the reaction having been carried out for 5 hours at 20° C. After the reaction was over, the residual gas was purged and the content of the tube was neutralized, washed with water and dried following the conventional steps. The results of ion-gas chromatography with FID while raising the temperature of the specimen of the thus obtained reaction product at a rate of 10° C./min are shown in Table 17 representing the weight ratio (in percentage) of the detected components.

Identification of each compound was carried by mass spectrometry and by $^1$H- and $^{19}$F-NMR, respectively.

TABLE 17

| Weight ratio (%) of the detected component | |
|---|---|
| Component | Weight ratio (%) |
| Benzene | 10.9 |
| (3,3,3-Trifluoropropyl)benzene | 59.5 |
| Bis(3,3,3-trifluoropropyl)benzene | 28.9 |
| Tris(3,3,3-trifluoropropyl)benzene | 0.7 |

By distilling the reaction mixture, i.e., the treated content of the reaction tube, (3,3,3-trifluoropropyl)benzene boiling at 155° to 157° C./760 mmHg and bis(3,3,3-trifluoropropyl)benzene boiling at 110° to 130° C./20 min mmHg were obtained.

What is claimed is:

1. A process for producing phenyl-[(3,3,3-trifluoropropyl)phenyl]methane, which comprises bringing (3,3,3-trifluoropropyl)benzene into reaction with benzyl chloride in the presence of an acid catalyst.

2. The process according to claim 1, wherein the acid catalyst is a member selected from the group consisting of aluminum trichloride, ferric chloride, antimony pentachloride, sulfuric acid, silica-alumina and synthetic zerolite.

* * * * *